US007116115B2

United States Patent
Gianchandani et al.

(10) Patent No.: US 7,116,115 B2
(45) Date of Patent: Oct. 3, 2006

(54) MICROMACHINED PROBE APPARATUS AND METHODS FOR MAKING AND USING SAME TO CHARACTERIZE LIQUID IN A FLUIDIC CHANNEL AND MAP EMBEDDED CHARGE IN A SAMPLE ON A SUBSTRATE

(75) Inventors: Yogesh B. Gianchandani, Ann Arbor, MI (US); Larry L. Chu, Madison, WI (US); Kenichi Takahata, Ann Arbor, MI (US); Ponnambalam Selvaganapathy, Freemont, CA (US); Juda L. Shohet, Madison, WI (US)

(73) Assignees: The Regents of the University of Michigan, Ann Arbor, MI (US); Wisconsin Alumni Research Foundation, Madison, WI (US)

(*) Notice: Subject to any disclaimer, the term of this patent is extended or adjusted under 35 U.S.C. 154(b) by 40 days.

(21) Appl. No.: 10/852,058

(22) Filed: May 24, 2004

(65) Prior Publication Data

US 2005/0017172 A1    Jan. 27, 2005

Related U.S. Application Data

(60) Provisional application No. 60/476,381, filed on Jun. 6, 2003.

(51) Int. Cl.
*G01R 27/26* (2006.01)
*G01R 31/02* (2006.01)
*G01R 31/302* (2006.01)

(52) U.S. Cl. .................. 324/661; 324/72; 324/72.5; 324/750

(58) Field of Classification Search ................ 324/661, 324/754, 109, 72.5, 72, 750
See application file for complete search history.

(56) References Cited

U.S. PATENT DOCUMENTS 4,673,231 A * 6/1987 McAnulty, Sr. ............. 439/587
5,742,172 A * 4/1998 Yasutake .................... 324/754

(Continued)

FOREIGN PATENT DOCUMENTS

WO    WO 03/033993 A1    4/2003

OTHER PUBLICATIONS

Anderson, J.R., et al., Theory of the Vibrating Condenser Converter and Application to Contact Potential Measurements, Australian Journal of Applied Science, 3, 201, 1952.

(Continued)

*Primary Examiner*—Vincent Q. Nguyen
*Assistant Examiner*—Amy He
(74) *Attorney, Agent, or Firm*—Brooks Kushman P.C.

(57) ABSTRACT

A micromachined probe apparatus and methods for making and using same to characterize liquid in a fluidic channel and map embedded charge in a sample on a substrate are provided. The probe apparatus includes an integrated scanning tip and a dither actuation mechanism. The actuation is achieved using a bent-beam electrothermal actuator, and the probe tip is insulated from the actuator with a wide isolation gap. The device is fabricated by a modified micro electro-discharge machining process which allows electrical isolation within the micromachined structure using an epoxy plug. The apparatus may be used to measure changes in the external surface potential of a microfluidic channel as a function of varying pH of liquid inside the channel. The apparatus also may be used to map embedded charge in a thin layer on a substrate, showing it to be suitable for monitoring microelectronics manufacturing processes.

12 Claims, 6 Drawing Sheets

U.S. PATENT DOCUMENTS

| | | | | |
|---|---|---|---|---|
| 5,789,666 | A | * | 8/1998 | Bayer et al. .................. 73/105 |
| 5,963,783 | A | * | 10/1999 | Lowell et al. ................. 438/17 |
| 6,139,759 | A | * | 10/2000 | Doezema et al. ............ 216/11 |
| 6,198,300 | B1 | * | 3/2001 | Doezema et al. ........... 324/762 |
| 6,586,699 | B1 | | 7/2003 | Gianchandani et al. .. 219/69.13 |
| 6,624,377 | B1 | | 9/2003 | Gianchandani et al. .. 219/69.17 |

OTHER PUBLICATIONS

Bergstrom, P.L., et al., Dielectric Membrane Technology for Conductivity and Work-Function Gas Sensors, IEEE International Conference on Sensors and Actuators (Transducers, 1995), Stockholm, Sweden, 1995, pp. 993-996.

Butt, H.J., Measuring Local Surface Charge Densities in Electrolyte Solutions with a Scanning Force Microscope, Biophysical Journal, 63(2), 1992, pp. 578-582.

Chu, L.L., et al., A Micromachined Kelvin Probe for Surface Potential Measurements in Microfluidic Channels and Solid-State Applications, IEEE International Conference on Sensors and Actuators (Transducers, 2003), Boston, USA, 2003, pp. 384-387.

Cismaru, C., et al., Relationship Between the Charging Damage of Test Structures and the Deposited Charge on Unpatterned Wafers Exposed to an Electron Cyclotron Resonance Plasma, Appl. Phys. Lett., 72(10), 1998, pp. 1143-1145.

Fang, S., et al., Thin-Oxide Damage from Gate Charging During Plasma Processing, IEEE Electron Dev. Lett., 13, 1992, p. 288.

Friedmann, J.B., et al., Plasma-Parameter Dependency of Thin-Oxide Damage from Wafer Charging During Electron-Cyclotron-Resonance Plasma Processing, IEEE Trans. Semic. Mfg., 10(1), 154, 1997.

Heinz, W.F., et al., Relative Surface Charge Density Mapping with the Atomic Force Microscope, Biophysical J., 76, 1999, pp. 528-538.

Hoff, A., et al., A Novel Approach to Monitoring of Plasma Processing Equipment and Plasma Damage Without Test Structures, IEEE/SEMI Advanced Semic. Manufacturing Conf., 185, 1997.

Hunter, Robert J., Introduction to Modern Colloid Science, Oxford Science Publications, 1993.

Ludeke, R., et al., Imaging of Oxide and Interface Charges in SiO2-Si, Microelectronic Engineering, 59, 2001, pp. 259-263.

Man, F., et al., Microfluidic Plastic Capillaries on Silicon Substrates: A New Inexpensive Technology for Bioanalysis Chips, IEEE MEMS, Nagoya, Japan, 1997, pp. 311-316.

Morita, S., et al., Defects and their Charge Imaging on Semiconductor Surfaces by Non-Contact Atomic Force Microscopy and Spectroscopy, J. Crystal Grth., 210, 2000, pp. 408-415.

Murphy, P.V., et al., Blood Compatibility of Polymer Electrets, Proc. Int. Conf. On Electrets, Charge Storage, and Transport in Dielectrics, Miami Beach, FL, Electrochemical Society, Princeton, NJ, 1973, pp. 627-649.

Nabban, W., et al., A High-Resolution Scanning Kelvin Probe Microscope for Contact Potential Measurements on the 100 nm Scale, Review of Scientific Instruments, 68(8), 1997, p. 3108.

Peterson, I.R., Kelvin Probe Liquid-Surface Potential Sensor, Review of Scientific Instruments, 70(8), Aug. 1999, pp. 3418-3424.

Que, L., et al., Bent-Beam Electro-thermal Actuators-I: Single Beam and Cascaded Devices, J. Microelectro-mech. Sys., 10(2), 2001, pp. 247-254.

Raiteri, R., et al., Measuring Electrostatic Double-Layer Forces at High Surface Potentials with the Atomic Force Microscope, Journal of Physical Chemistry, 100, 1996, pp. 16700-16705.

Surplice, N.A., et al., A Critique of the Kelvin Method of Measuring Work Functions, J. Physics E: Scientif. Instrum. 3, 477, 1970.

Takahata, K., et al., Batch Mode Micro-electro-discharge Machining, J. Microelectromech. Syst., 11(2), 2002, pp. 102-110.

* cited by examiner

MICROMACHINED PROBE APPARATUS AND METHODS FOR MAKING AND USING SAME TO CHARACTERIZE LIQUID IN A FLUIDIC CHANNEL AND MAP EMBEDDED CHARGE IN A SAMPLE ON A SUBSTRATE

CROSS-REFERENCE TO RELATED APPLICATION

This application claims the benefit of U.S. provisional application Ser. No. 60/476,381, filed Jun. 6, 2003.

STATEMENT REGARDING FEDERALLY SPONSORED RESEARCH OR DEVELOPEMENT

This invention was made with Government support from DARPA under Grant No. 040074 and from NSF under Grant Nos. 043898 and DMR-0084402. The Government has certain rights in the invention.

BACKGROUND OF THE INVENTION

1. Field of the Invention

This invention relates to a micromachined probe apparatus and methods for making and using same to characterize liquid in a fluidic channel and map embedded charge in a sample on a substrate.

2. Background Art

U.S. Pat. Nos. 6,624,377 and 6,586,699 are related to the present application.

The following references are referred to in this specification:

| | |
|---|---|
| [And52] | J. R. Anderson et al., "Theory of the Vibrating Condenser Converter and Application to Contact Potential Measurements," AUSTRALIAN JOURNAL OF APPLIED SCIENCE, 3, 201, 1952. |
| [Ber95] | P. L. Bergstrom et al., "Dielectric Membrane Technology for Conductivity and Work-Function Gas Sensors," IEEE INTERNATIONAL CONFERENCE ON SENSORS AND ACTUATORS (Transducers, 1995), Stockholm, Sweden, pp. 993–996, 1995. |
| [But92] | H. -J. Butt, "Measuring Local Surface Charge Densities in Electrolyte Solutions with a Scanning Force Microscope," BIOPHYSICAL JOURNAL, 63(2), pp. 578–582, 1992. |
| [Chu03] | L. L. Chu et al., "A Micromachined Kelvin Probe for Surface Potential Measurements in Microfluidic Channels and Solid-State Applications," IEEE INTERNATIONAL CONFERENCE ON SENSORS AND ACTUATORS (Transducers, 2003), Boston, USA, pp. 384–387, 2003. |
| [Cis98] | C. Cismaru et al., "Relationship Between the Charging Damage of Test Structures and the Deposited Charge on Unpatterned Wafers Exposed to an Electron Cyclotron Resonance Plasma," APPL. PHYS. LETT., 72(10), pp. 1143–1145, 1998. |
| [Fan92] | S. Fang et al., "Thin-Oxide Damage from Gate Charging During Plasma Processing," IEEE ELECTRON DEV. LETT., 13, p. 288, 1992. |
| [Fri97] | J. B. Friedmann et al., "Plasma-Parameter Dependency of Thin-Oxide Damage from Wafer Charging During Electron-Cyclotron-Resonance Plasma Processing," IEEE TRANS. SEMIC. MFG., 10(1), 154, 1997. |
| [Hei99] | W. F. Heinz et al., "Relative Surface Charge Density Mapping with the Atomic Force Microscope," BIOPHYSICAL J., 76, pp. 528–538, 1999. |
| [Hof97] | A. Hoff et al., "A Novel Approach to Monitoring of Plasma Processing Equipment and Plasma Damage Without Test Structures," IEEE/SEMI ADVANCED SEMIC. MANUFACTURING CONF., 185, 1997. |
| [Hun93] | Robert J. Hunter, "Introduction to Modern Colloid Science," OXFORD SCIENCE PUBLICATIONS, 1993. |
| [Lud01] | R. Ludeke et al., "Imaging of Oxide and Interface Charges in SiO2-Si," MICROELECTRONIC ENGINEERING, 59, pp. 259–263, 2001. |
| [Man97] | F. Man et al., "Microfluidic Plastic Capillaries on Silicon Substrates: A New Inexpensive Technology for Bioanalysis Chips," IEEE MEMS, Nagoya, Japan, pp. 311–316, 1997. |
| [Mor00] | S. Morita et al., "Defects and their Charge Imaging on Semiconductor Surfaces by Non-Contact Atomic Force Microscopy and Spectroscopy," J. CRYSTAL GRTH., 210, pp. 408–415, 2000. |
| [Mur73] | P. V. Murphy et al., "Blood Compatibility of Polymer Electrets," PROC. INT. CONF. ON ELECTRETS, CHARGE STORAGE, AND TRANSPORT IN DIELECTRICS, Miami Beach, FL, Electrochemical Society, Princeton, NJ, pp. 627–649, 1973. |

-continued

| | |
|---|---|
| [Nab97] | W. Nabhan et al., "A High-Resolution Scanning Kelvin Probe Microscope for Contact Potential Measurements on the 100 nm Scale," REVIEW OF SCIENTIFIC INSTRUMENTS, 68(8), p. 3108, 1997. |
| [Pet99] | I. R. Peterson, "Kelvin Probe Liquid-Surface Potential Sensor," REVIEW OF SCIENTIFIC INSTRUMENTS, 70(8), pp. 3418–3424, Aug. 1999. |
| [Que01] | L. Que et al., "Bent-Beam Electro-thermal Actuators-I: Single Beam and Cascaded Devices," J. MICROELECTROMECH. SYS., 10(2), pp. 247–254, 2001. |
| [Rai96] | R. Raiteri et al., "Measuring Electrostatic Double-Layer Forces at High Surface Potentials with the Atomic Force Microscope," JOURNAL OF PHYSICAL CHEMISTRY, 100, pp. 16700–16705, 1996. |
| [Sur70] | N. A. Surplice et al., "A Critique of the Kelvin Method of Measuring Work Functions," J. PHYSICS E: SCIENTIF. INSTRUM. 3, 477, 1970. |
| [Tak02] | K. Takahata et al., "Batch Mode Micro-electro-discharge Machining," J. MICROELECTROMECH. SYS., 11(2), pp. 102–110, 2002. |

The vibrating Kelvin probe is an effective, non-invasive tool for the non-contact mapping of surface potentials [And52, Sur70, Nab97]. Since surface potential includes a component due to work function and another due to trapped charge, this tool can be used to map either quantity on a surface when the other is kept uniform. For example, trapped charge is monitored in semiconductor IC-fabrication because it has been correlated to the degradation of the device parameters. This function can be performed by mapping the contact (or surface) potential difference (CPD) between a probe and the sample wafer [Hof97]. Since the Kelvin probe method is a non-contact and non-destructive diagnostic, it can be used to monitor processes that are known to introduce trapped charges in wafers, such as plasma etch and deposition, ion implantation, and certain cleaning and wafer drying operations. Conventional plasma damage characterization approaches [Fri97, Cis98, Fan92] are based on electrical or surface analytical techniques, which cannot measure local charge distributions on patterned wafers. The ability to measure local charge distributed across patterns on production wafers can be a critical asset in predicting yield and longevity of devices.

Another potential application for scanning Kelvin probes is the mapping of surface charge in a biofluidic channel or tube [Bai98]. Charge distribution on the wall, acquired during manufacturing or in routine operation, can impact the function and behavior of the fluid in the channel. For example, it has been linked to cell adhesion and clotting of red blood cells on artificial surfaces [Mur73]. A Kelvin probe can be used to map the charge embedded in the wall by scanning the outside of the fluidic channel using the electrolyte in the channel as an electrode. A macro-scale Kelvin probe has also been used to measure the surface potentials of organic overlayers on poorly conducting liquid substrates [Pet99], and a micromachined device based on this principle has been developed for gas sensing [Ber95].

Relative surface charge density has been measured suing atomic force microscopy (AFM) in an aqueous electrolytic ambient [But92, Rai96, Hei99]. When the AFM tip is in close proximity to the sample, the electrostatic force produced by their overlapping electrical double layers is detected by the AFM tip and correlated to charge density. This method is effective for measurements of biological samples in an aqueous environment. In non-aqueous environments, non-contact AFM methods have recently been used for the mapping of surface [Mor00] and interface [Lud01] charge on a semiconductor. However, these experiments require ultra high vacuum (UHV) and, in some cases, cooling of the system to liquid He temperature, which limit their application.

SUMMARY OF THE INVENTION

An object of the present invention is to provide an improved micromachined probe apparatus and methods for making and using same to characterize liquid in a fluidic channel and map embedded charge in a sample on a substrate.

In carrying out the above object and other objects of the present invention, a micromachined probe apparatus for measuring surface potential of a sample in a non-invasive manner is provided. The apparatus includes a micromachined probe electrode having a probe tip disposed at a distal end thereof. An electrical signal is provided based on surface potential of the sample when separation between the probe tip and the sample is varied. The probe tip and the sample form a capacitor having a capacitance. A micromachined actuator moves the probe electrode relative to the sample in response to an electrical drive signal to vary the separation which varies the capacitance. A dielectric part mechanically connects but electrically insulates the actuator and the probe electrode. The dielectric part decouples the electrical drive signal and the provided electrical signal from each other.

The actuator may vibrate the probe electrode.

The apparatus may be a planar structure, which may include a conductive foil.

The actuator and the probe electrode may be formed by removing material from a sheet of material.

The sheet of material may include conductive foil, and the probe electrode and the actuator may be formed by electric discharge machining the conductive foil.

The apparatus may further include a substrate for supporting the actuator thereon.

The apparatus may further include a signal lead connected to the probe electrode for conducting the provided electrical signal from the probe electrode.

The apparatus may further include an electrical circuit coupled to the signal lead to measure the conducted electrical signal.

The electrical circuit may include a variable bias adjusted so that substantially no current flows between the sample and the probe electrode. The adjusted bias may provide an indication of the surface potential of the sample.

The actuator may include an electrothermal actuator.

The electrothermal actuator may be a bent-beam electrothermal actuator.

The dielectric part may include an epoxy plug.

Further in carrying out the above object and other objects of the present invention, a method of mapping embedded charge in a sample formed on a substrate in a non-invasive manner is provided. The method includes positioning a micromachined probe apparatus adjacent to the sample so that the probe tip and the sample form a capacitor having a capacitance. The apparatus includes a probe electrode having a probe tip disposed at a distal end thereof, an actuator for moving the probe electrode relative to the sample, and a dielectric part which mechanically connects but electrically insulates the actuator and the probe electrode. The sample is scanned with the apparatus to generate a plurality of electrical signals based on the embedded charge in a scanned portion of the sample. A map is generated of the embedded charge in the scanned portion of the sample based on the electrical signals.

The method may further include varying separation between the sample and the probe tip with the actuator to vary the capacitance.

Yet still further in carrying out the above object and other objects of the present invention, a method of characterizing a fluid contained in a fluidic channel in a non-invasive manner is provided. The method includes positioning an electrode adjacent to a wall of the channel wherein the electrode and the wall are movable relative to one another, and separation is varied between the electrode and the wall to generate or modulate an electrical signal.

The generated or modulated electrical signal may represent surface potential of the wall with respect to the electrode and the fluid.

The electrode may be a probe electrode integrated on a first substrate and the channel may be integrated on a second substrate different from the first substrate.

Still further in carrying out the above object and other objects of the present invention, a method of making a micromachined probe apparatus is provided. The method includes: providing a conductive sheet of material, removing material from the sheet of material to form a hole in the sheet of material, filling the hole with a dielectric material, and removing material from the sheet of material to form a probe electrode and an actuator. The dielectric material forms a dielectric part which mechanically connects but electrically insulates the actuator and the probe electrode.

The steps of removing may be performed by electric discharge machining the conductive sheet.

The method may further include the step of removing material from the sheet of material to form a signal lead connected to the probe electrode.

The dielectric material may be an epoxy, and the method may further include the step of curing the epoxy after the step of filling.

The method may further include attaching the actuator to a substrate.

The probe electrode may have a probe tip disposed at a distal end thereof.

The method may further include attaching a probe tip at a distal end of the probe electrode.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIGS. 4a, 4c, 4e, 4g, 4i and 4k are top plan schematic views of a sheet of metal that is micromachined in a µEDM fabrication sequence to form the apparatus having a dielectric plug which provides electrical isolation; FIGS. 4b, 4d, 4f, 4h, 4j and 4l are sectional schematic views of the FIGS. 4a, 4c, 4e, 4g, 4i and 4k, respectively, wherein FIGS. 4a and 4b show a stock metal sheet, FIGS. 4c and 4d show EDM plug definition, FIGS. 4e and 4f show epoxy fill and cure; FIGS. 4g and 4h show lapping; FIGS. 4i and 4j show an EDM microstructure; and FIGS. 4k and 4l show a finished microstructure;

DETAILED DESCRIPTION OF THE PREFERRED EMBODIMENTS

One embodiment of a micromachined probe apparatus constructed in accordance with the present invention and described herein can be used for many purposes including, but not limited to, mapping surface charge and measuring CPD. The device or apparatus generally include an actuator which provides axial dither motion, a sense probe, which is electrically isolated from the actuator, and a lead transfer beam for the probe electrode. A wide isolation region is important to minimize capacitive coupling between the drive signal of the actuator and probe. An insulating glass substrate also helps in this regard, as does the choice of actuator. The bent-beam actuator is electrothermally driven by passing current through the bent beam, which amplifies the resulting deformation into an outward motion of the probe tip [Que01]. It is selected because it offers non-resonant dither motion with amplitude in the 10 μm range with drive voltages of a few volts. The low voltage minimizes the coupling of the drive signal to the sense probe, while the large amplitude non-resonant displacement permits the dithering frequency and amplitude to be varied to suit the needs of the measurement. For measurements made along micromachined capillary channels, the electrical ground is provided by the conductive liquid present in the channel. However, the low conductivity of the liquid, and the long and narrow shape of the channel can make the access resistance to the point of measurement large, and create a slow RC time constant. To accommodate this, the dither frequency of the Kelvin probe is kept low.

Concept and Design

The Kelvin probe method, which can be applied at room temperature and pressure, uses a vibrating capacitor to measure CPD. The concept is as follows: when two disconnected surfaces such as the probe and the sample are brought into close proximity, the vacuum levels are aligned. In electrical contact (which does not occur during the normal operation of the probe), the Fermi levels are aligned at equilibrium. Electron flow is necessary for the equilibrium to be achieved. As a result of this flow, the surface with the larger work function acquires a negative charge, and the other a positive one. An external bias may be used to compensate the electric field resulting from this charge transfer. When the system reaches equilibrium, the resulting potential difference is the contact potential difference in the CPD:

$$V_{CPD} = \Phi_{12} = \Phi_1 - \Phi_2 + \Phi_D \quad (1)$$

where $\Phi_1$ and $\Phi_2$ are the work functions of the sample and the probe tip, respectively, and $\Phi_D$ is the potential due to trapped charge that may exist on their surfaces. As the probe, which is biased at $-V_b$ with respect to the sample, is dithered in close proximity to it, an AC current is induced by the modulation of the capacitance ($C_K$) between them:

$$i = (V_{CPD} + V_b) \cdot (dC_K dt) \quad (2)$$

Figure 1:
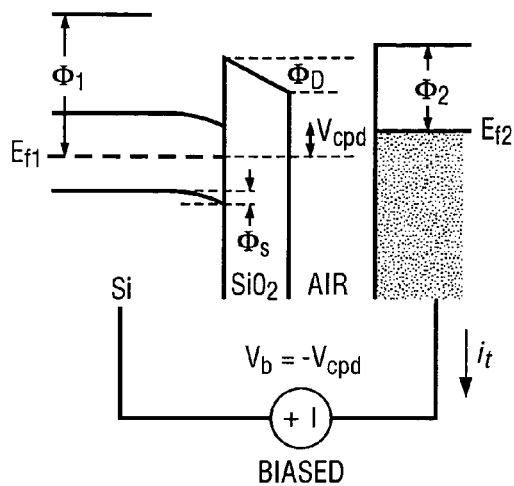
FIG. 1 is an energy band diagram for a system having a sample with a charged oxide layer on a silicon substrate with applied bias that results in zero electric field in an air gap.

Theoretically, $V_b$ is varied until the current goes to zero to determine $V_{CPD}$. In practice, the noise-limited rms current is monitored, and the bias which minimizes it is $-V_{CPD}$. This arrangement is illustrated for a semiconductor sample and metal probe in FIGS. 1 and 2. In this situation, there is an additional potential drop of $\Phi_S$ in the semiconductor, which must be added to the right-hand side of Equation (1). In most situations, however, the magnitude of $\Phi_S$ is relatively small.

Figure 3:
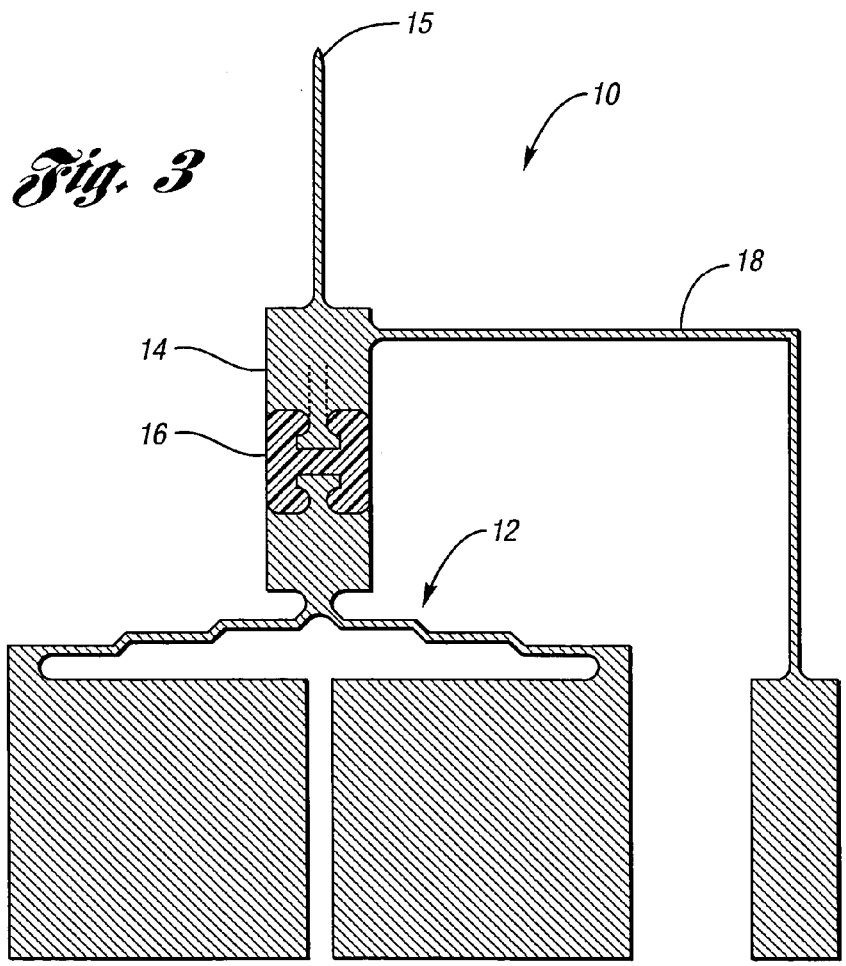
FIG. 3 is a schematic view of a µEDM Kelvin probe device or apparatus constructed in accordance with one embodiment of the present invention.

Referring next to FIG. 3, in one embodiment of the present invention, the apparatus, generally indicated at 10, includes an actuator 12 which provides the axial dither motion, a sense probe or electrode 14 with a tip 15, which is electrically isolated from the actuator 12 by a dielectric part or plug 16, and a lead transfer beam or lead 18 for the probe electrode 14. A wide isolation region is important to minimize capacitive coupling between the drive signal of the actuator 12 and the probe electrode 14. An insulating glass substrate (not shown) also helps in this regard, as does the choice of actuator.

Figure 8:
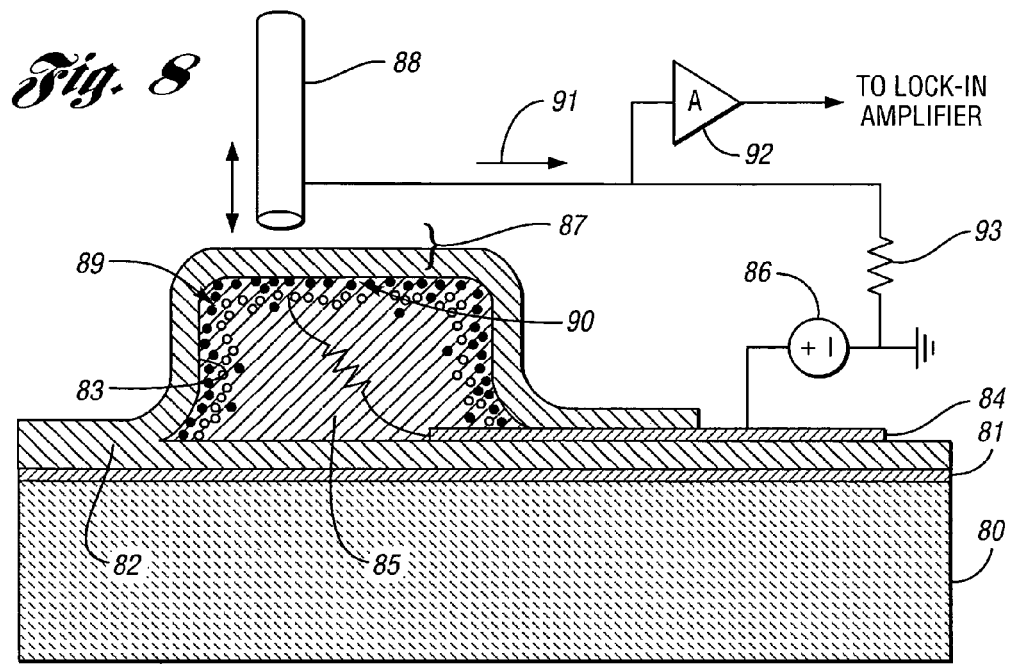
FIG. 8 is a sectional, schematic view of one embodiment of the apparatus of the present invention measuring surface potential in a device having a microfluidic channel.

The bent-beam actuator 12 is electrothermally driven by passing current through its bent beam, which amplifies the resulting deformation into an outward motion of the tip 16 [Que01]. It is selected because it offers non-resonant dither motion with amplitude in the 10 μm range with drive voltages of a few volts. The low voltage minimizes the coupling of the drive signal to the sense probe 14, while the large amplitude non-resonant displacement permits the dithering frequency and amplitude to be varied to suit the needs of the measurement. For measurements made along micromachined capillary channels (as shown in FIG. 8), the electrical ground is provided by the conductive liquid present in the channel. However, the low conductivity of the liquid, and the long and narrow shape of the channel can make the access resistance to the point of measurement large, and create a slow RC time constant. To accommodate this, the dither frequency of the Kelvin probe is kept low.

Fabrication

The micromachined Kelvin probe apparatus 10 is preferably fabricated by a modified micro electro-discharge machining (μEDM) process. This technique is attractive because it can be used to fabricate parts from any electrically conductive material. Batch mode μEDM, performed with electroplated arrays of electrodes, offers very high throughput [Tak02]. However, normal μEDM by itself does not allow electrical isolation since all the mechanically connected features are also electrically connected. In the case of the micromachined Kelvin probe apparatus 10, the probe tip 15 must be isolated from the dithering actuator 12, preferably, by a large width of isolation to minimize the capacitive feed-through of the drive signal. This provides the motivation for the modified process described below.

Figure 4:
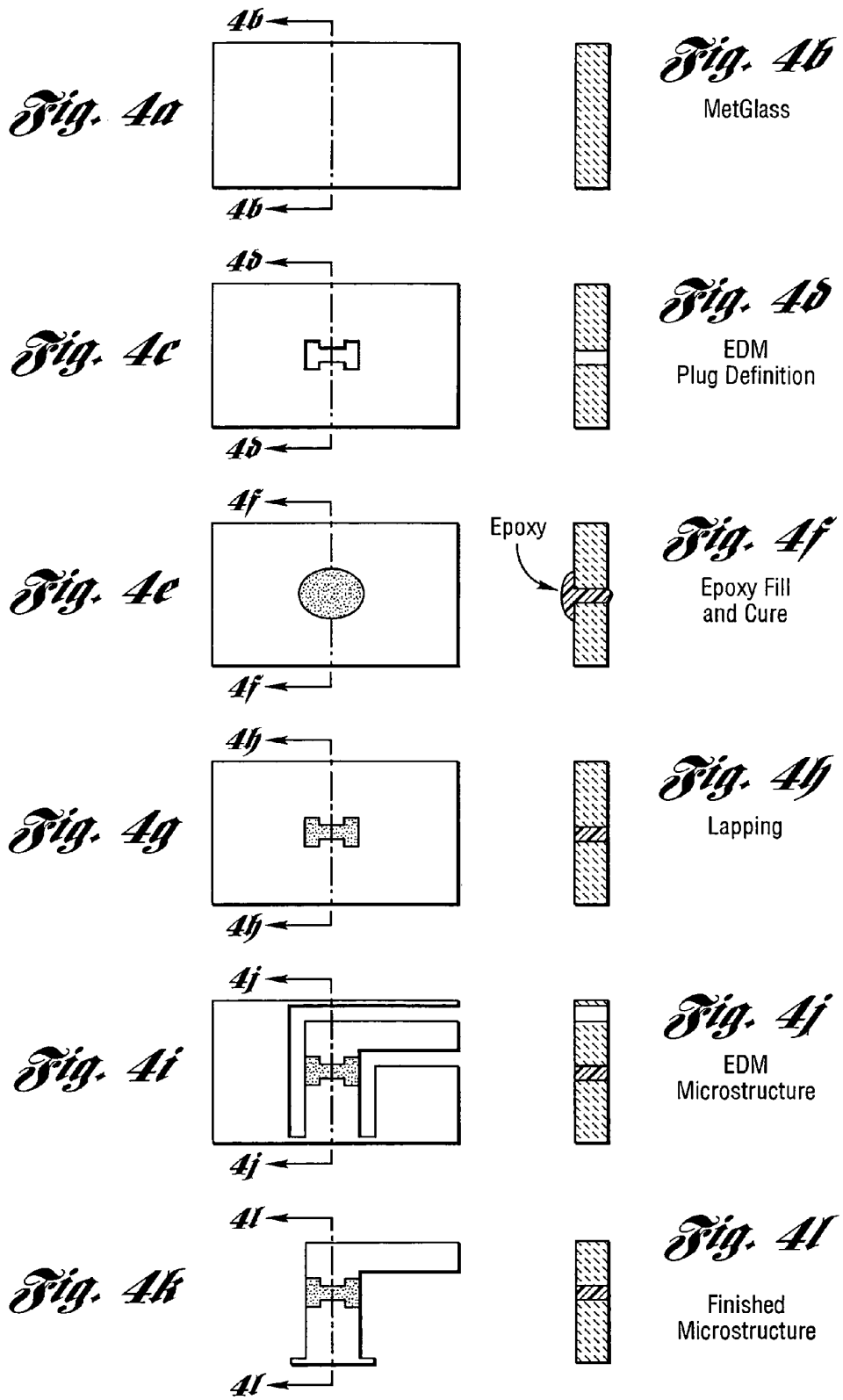

The starting material is a commercially available 30 μm thick stock metal sheet of MetGlas 2826MB; it is an alloy of primarily Ni and Fe (FIGS. 4a and 4b). First, a traditional μEDM step is performed to form a hole which defines the shape of the epoxy plug 16 in the workpiece (FIGS. 4c and 4d). The piece is removed from the μEDM oil bath and cleaned in an ultrasonic bath with detergent. A quick-hardening, two-part epoxy is properly mixed and applied onto the machined workpiece to fill the hole (FIGS. 4e and 4f). The epoxy is allowed to cure for over 12 hours to achieve proper mechanical stiffness and adhesion. A lapping step is performed for both sides of the workpiece to remove the excess cured epoxy (FIGS. 4g and 4h). The workpiece is cleaned before returning to the μEDM machine for the definition of the rest of the microstructure with the rest of the features aligned to the epoxy plug 16, which is released by cutting along its edges (FIGS. 4i and 4j). Finally, the finished part is attached to a substrate (not shown) for testing (FIGS. 4k and 4l). A glass substrate is used to minimize parasitic capacitance that might cause the sensed signal to leak away.

In a variant of the apparatus, a larger Kelvin probe tip is attached onto the micromachined device for use with a sample which has coarse spatial variation and weak Kelvin probe signals. The larger tip has an area of 0.01 mm$^2$ and is made of tungsten.

Experimental Results

Figure 5:
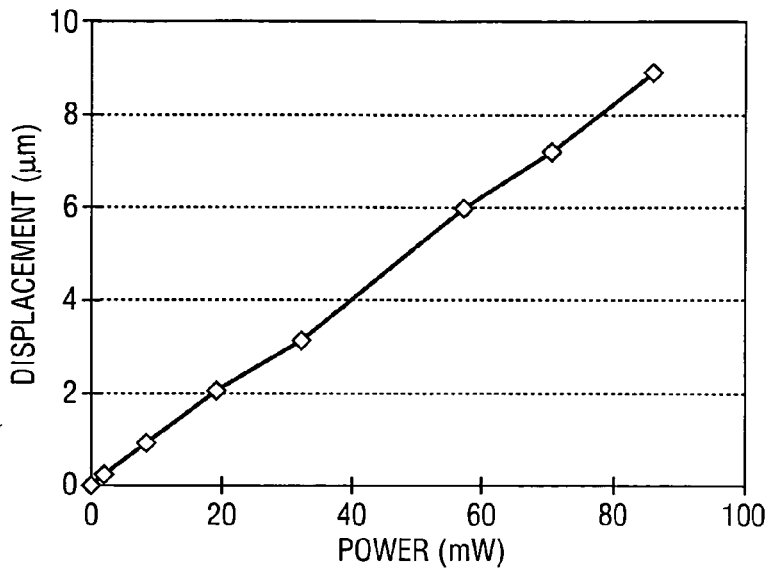
FIG. 5 is a graph of probe tip displacement versus power which illustrates the response of one embodiment of a electro-thermal actuator of the present invention.

The operation of the integrated electro-thermal actuator 12 is verified by supplying a current for actuation and monitoring the displacement of the tip 15 using a calibrated optical method. The actuator 12 generated a maximum displacement of 9 μm when actuated at 85 mW with a resistance of 4.2 Ω (FIG. 5). The actuator satisfies the displacement requirements for a scanning Kelvin probe since <5 μm of displacement is sufficient.

The Kelvin probe signal is a very small current signal related to the dither actuation. If a parallel plate approximation is used for the capacitance between the probe and sample, the signal amplitude is:

$$i = (V_{CPD} + V_b) \cdot \frac{dC_K}{dt} = 2 \cdot f \cdot (V_{CPD} + V_b) \cdot \varepsilon \cdot A \cdot \left( \frac{1}{g_0 - g_a} - \frac{1}{g_0} \right) \quad (3)$$

where f is the actuation frequency, $\varepsilon$ is the permittivity of the medium (air), A is the tip capacitor area, $g_0$ is the initial capacitor gap, and $g_a$ is the actuation displacement. Assuming a tip area of 0.01 mm$^2$, $V_{CPD}$=1 V, actuation frequency of 13 Hz, and a capacitive gap of 5 µm (with 50% gap modulation due to actuation), the tip current is in the order of 500 fA. Hence, it is important to minimize noise from the measurement setup and electronics.

Figure 2:
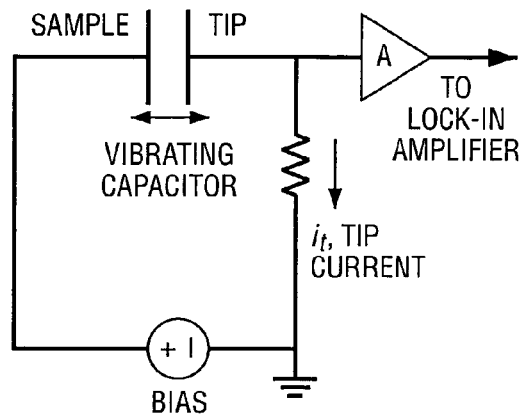
FIG. 2 is a simplified circuit diagram for the system of FIG. 1.
Figure 6:
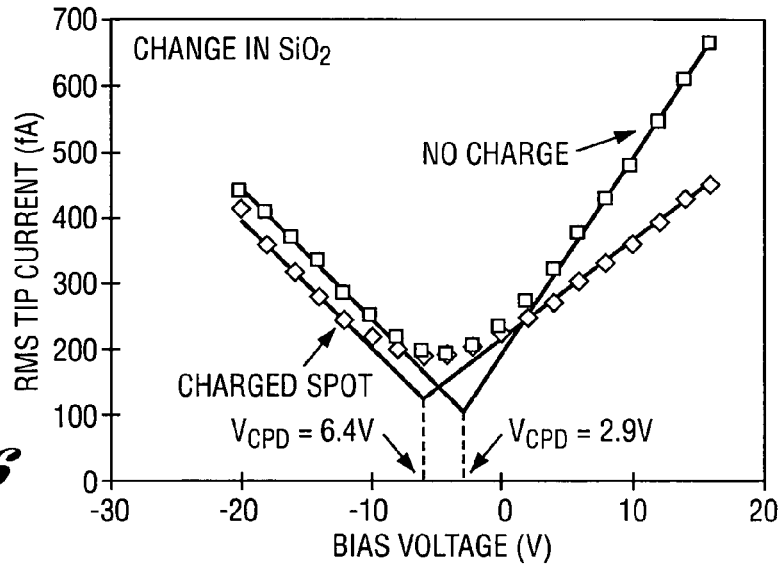
FIG. 6 is a graph of two Kelvin probe traces that demonstrate how the RMS tip current can be interpreted to obtain the CPD.
Figure 7:
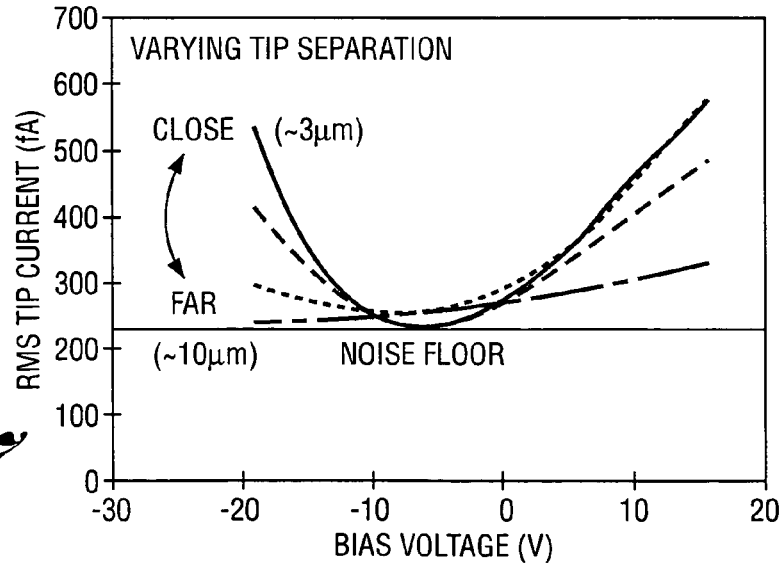
FIG. 7 is a graph which illustrates the Kelvin probe signal obtained at different gap separations; this indicates that when the gap is too large, the signal is not reliable.

The current signal is fed through a transconductance amplifier (SR570) set a 1 V/pA and then detected with a lock-in amplifier (SR830 DSP) that is frequency locked to the actuation frequency. The current sensing resistance shown in FIG. 2 is inside the instrument, which has a virtual ground at its input and an equivalent input impedance of 1 MΩ; using an actual resistor for current sensing would have produced an unacceptable level of Johnson noise due to the large resistance necessary to sense such small currents. The actuation frequency is carefully selected to avoid harmonics and sub-harmonics of common noises such as 60 Hz power line interference. With the tip 15 close to the sample (~5 µm), dither amplitudes of 2–4 µm are typical. The lock-in amplifier essentially provides the rms probe current signal strength. The measured rms probe current as a function of $V_b$ is compared for two locations on a charged sample in FIG. 6. These results were obtained with a tungsten tip with a sense area of 0.01 mm$^2$, and a 13 Hz dither. As shown, the $V_{CPD}$ should be extrapolated from tangents drawn to the response curve at high bias values, because at low currents the amplifier noise and parasitic feed through from the drive signal can dominate even after carefully minimizing these effects. Essentially, the expected triangular-shaped response of rms current magnitude is superimposed on a noise floor of approximately 150–200 fA. When the tip-to-sample separation is changed, the slope of current-to-bias response curve changes (FIG. 7). Artifacts from this are eliminated by keeping the tip-sample separation constant during a scan. Generally, this means that the slope of the rms tip current to $V_b$ should be the same for all readings.

The measurement setup for the microfluidic tests is shown in FIG. 8. A substrate 80 has an oxide layer 81 formed thereon. A parylene layer 82 forms a microfluidic channel 83. A gold electrode 84 is formed on the layer 82 and extends into the channel 83. The electrode 84 is coupled to the liquid 85 in the channel 83 wherein the liquid 85 forms an electrode. The gold electrode 84 is also coupled to a bias source 86.

A vibrating capacitor, generally indicated at 87, includes a top wall of the layer 82 and a SKP vibrating tip 88. An electrical double layer (EDL) is indicated at 89 and surface charge is indicated at 90. Tip current flows in the direction of arrow 91 to an amplifier 92 and a resistor 93 also coupled to the bias source 86.

As earlier mentioned, electrical access to the interior of the channel 83 is provided through the Au electrode 84 that is in contact with the fluid 85 inside the channel 83 but does not extend along its full length.

Figure 9:
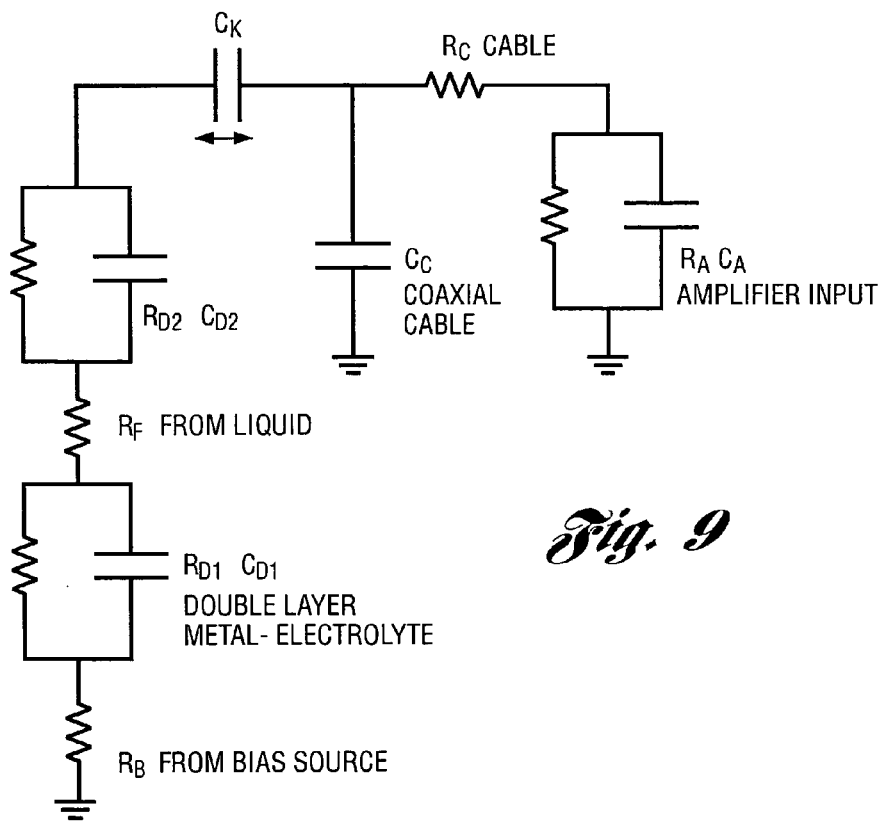
FIG. 9 is a circuit diagram illustrating an equivalent circuit corresponding to FIG. 8.

The electrical equivalent circuit is shown in FIG. 9; the Kelvin probe capacitance is $C_K$, while $R_C$ and $C_C$ are due to the coaxial cable from the probe tip 88 to the amplifier 92, which has an input impedance of $R_A$ and $C_A$. Also, $R_B$ is the internal resistance of the biasing DC source 86 together with the cable resistance from the biasing source 86 to the conductor 84 inside the channel 83. These components are not affected when the pH of the liquid in the channel 83 is changed. On the other hand, several components are strongly affected by change in pH, and they are: $R_{D1}$, $C_{D1}$ and $R_{D2}$, $C_{D2}$ are the capacitance and parallel resistance of the double layer 89 at the electrolyte-metal and electrolyte-polymer interfaces [Hun93], respectively, and the fluid between the two double layers 89 can be modeled as simply a resistance, $R_F$. Due to the large input impedance of the amplifier 92, the cable resistances, $R_B$, $R_C$ can be ignored. The parallel resistances of the double layer 89 can be ignored as well since these values are typically very large. A change in the pH can be sensed from its impact on the double layer capacitances. The change in fluid resistance, $R_F$, is not significant because it is small compared to the impedance of the Kelvin probe capacitance, $C_K$.

Figure 10:
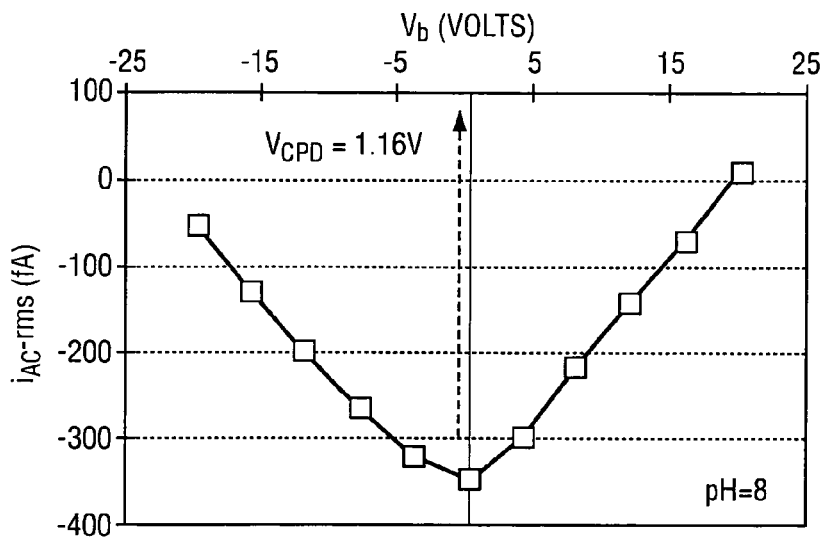
FIG. 10 is a graph of measured sense current amplitude, $I_{ac\text{-}rms}$, at a single spot above the microchannel of FIG. 8 with a top sample spacing of about 5 µm and a dither amplitude of about 2 µm.
Figure 11:
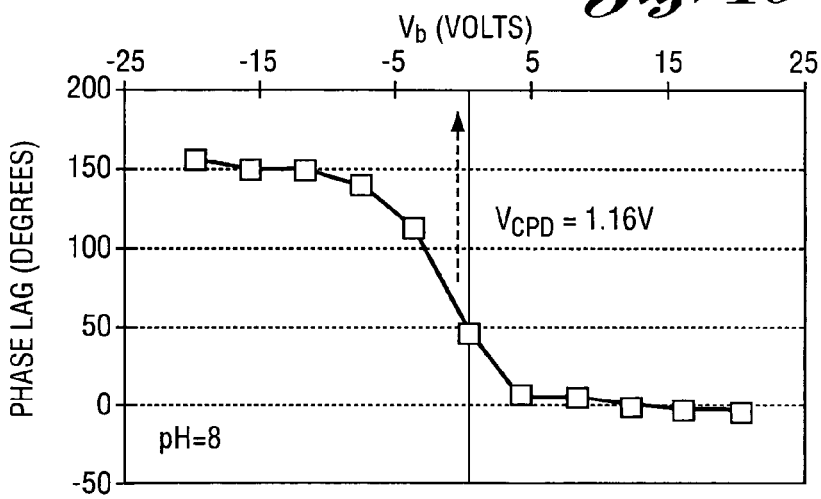
FIG. 11 is a graph of measured phase lag which corresponds to the same conditions as in FIG. 10.
Figure 12:
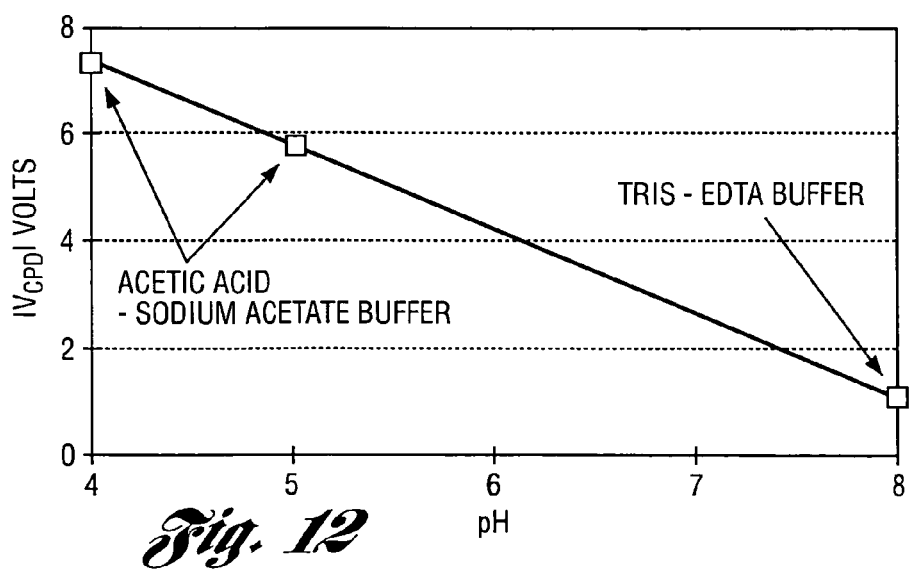
FIG. 12 is a graph of measured $V_{CPO}$ versus pH which shows the linear dependence of the two variables.

The measured sense current for a pH 8 buffer is shown in FIGS. 10 and 11. Both the magnitude (i.e., FIG. 10) and phase (i.e., FIG. 11) responses can provide the $V_{CPD}$. In the former, the lowest point is used to determine the contact potential, whereas in the phase plot, the point of maximum slope could be used. Experiments were performed to determine the relationship between the $V_{CPD}$ above a single point of the microchannel and the pH of the solution within it. The contact potentials for three different cases are plotted in FIG. 12, showing that the relationship is essentially linear. Acetic acid-sodium acetate and Tris-EDTA buffer systems are used to ensure that the pH in the channel is uniform and not affected by local residues when the system is flushed. A contact potential difference of ≈6 V is measured for a change in pH from 4 to 8 within the channel.

As described above, a new approach for the measurement of pH of fluids contained in microchannels is provided. Microfluidic systems are being widely developed for a number of biomedical applications ranging from glucose monitoring to DNA analysis and proteomics. For a number of applications, it is potentially useful to be able to measure the pH of the liquids within the microchannels. The vibrating electrode external to the channel can be used to measure changes in surface potential, which are correlated to pH. The vibrating electrode may be integrated onto the fluidic chip or could be a separate part.

Figure 13:
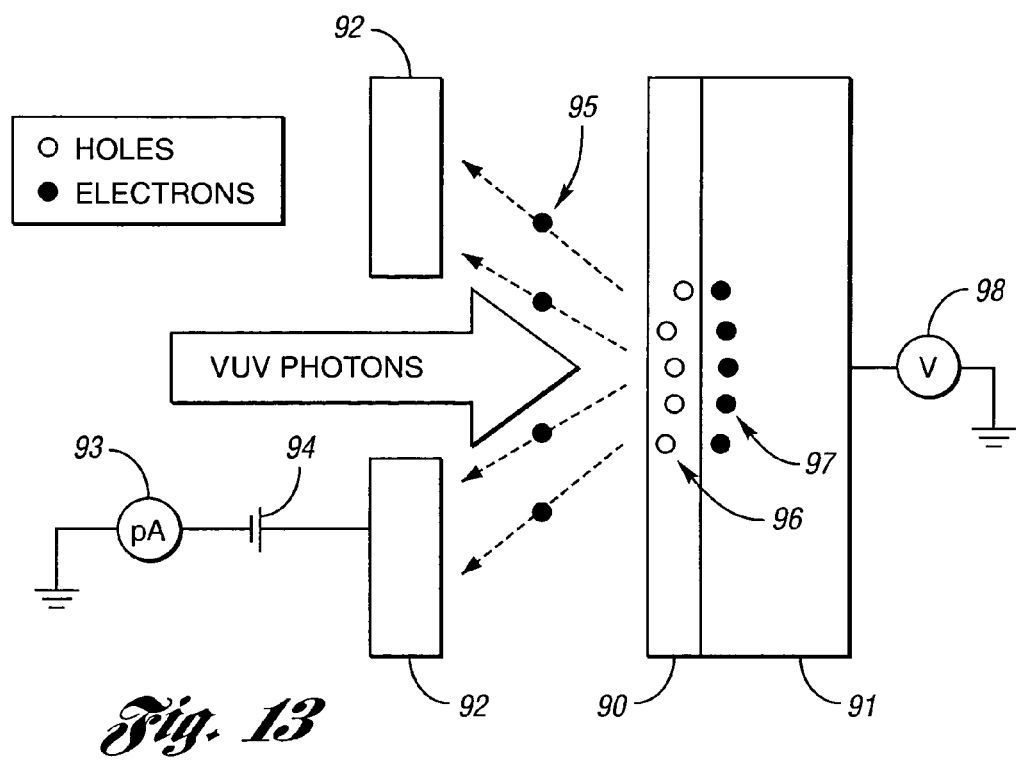
FIG. 13 is a schematic view which illustrates charging during IC fabrication and which is emulated by exposing an Si wafer with 359 nm thick oxide to vacuum UV synchrotron radiation.

As indicated previously, the Kelvin probe can be used to map charge distribution over a sample surface area. This is useful in a number of contexts, particularly in assessing plasma implantation and vacuum ultraviolet (VUV) photoemission. In order to evaluate the capability of the fabricated Kelvin probes in this regard, a test wafer was exposed to VUV radiation from a synchrotron to mimic charging due to photoemission during IC fabrication, as shown in FIG. 13.

A dielectric layer 90 of SiO$_2$ is formed on a conductive silicon substrate 91. VUV photons cause the emission of photoelectrons 95 which are detected by photoelectron collectors 92, which are coupled to grounded ammeters 93 through a bias source 94. Hole space charge 96 and compensating charge 97 are formed in the layer 90 and the substrate 91, respectively, which is coupled to an electrometer 98.

Figure 14:
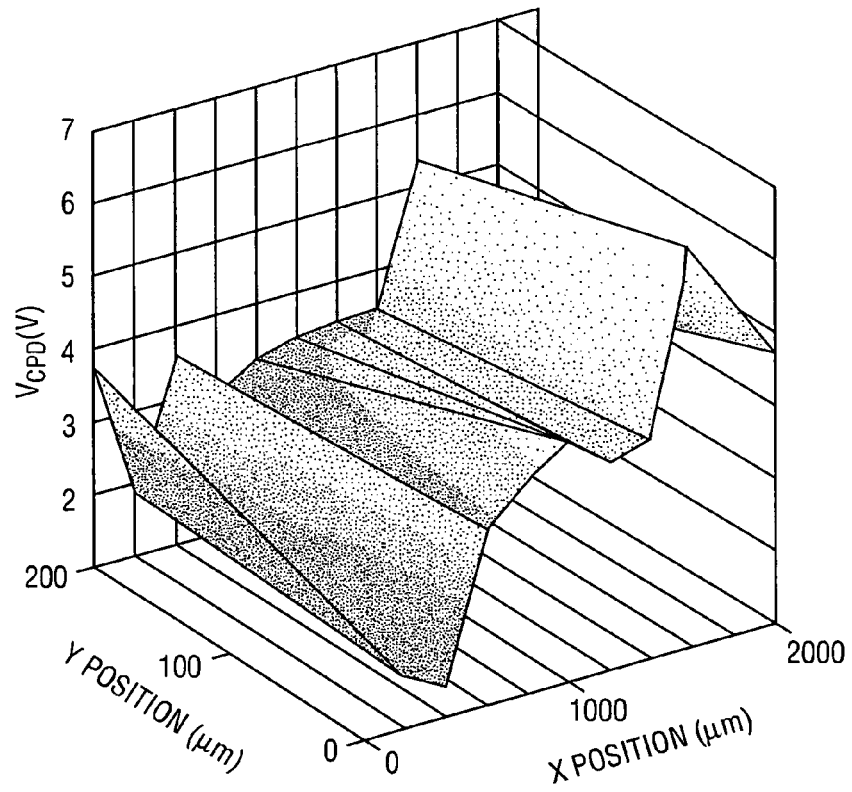
FIG. 14 is a 3-D graph or areal map of the resulting $V_{CPD}$ showing a portion of the exposed region.

FIG. 14 shows the areal distribution of $V_{CPD}$ on a charged sample that is obtained by exposing an Si wafer with 359 nm thick oxide to VUV radiation. Spatial variation of $V_{CPD}$ from 1–7 V over a few hundred microns is evident. The position of the peak corresponds to the center of the VUV exposure.

Conclusions

An embodiment of a micromachined Kelvin probe device or apparatus constructed with an integrated dither actuator is provided herein. The electrothermal actuator can achieve 9 µm displacement when actuated at 85 mW. The Kelvin probe tip is electrically isolated from the actuator using a modified µEDM process that permits wide expanses of dielectric materials to be embedded in the structure. The device has been successfully used to measure the 2-D charge variation in $SiO_2$ on a Si substrate and solution variations of pH in a microfluidic channel.

As described herein, the relatively simple microstructure can be used to provide surface potential measurements in a non-invasive manner, which are useful in both semiconductor and microfluidic diagnostics. In the latter context, it is possible to envision a microfluidic system with a Kelvin probe integrated above important positions in the channel, permitting integrated in-line measurements in real-time to control chemical reactions.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A micromachined probe apparatus for measuring surface potential of a sample in a non-invasive manner, the apparatus comprising:
   a micromachined probe electrode having a probe tip disposed at a distal end thereof and providing an electrical signal based on surface potential of the sample when separation between the probe tip and the sample is varied, the probe tip and the sample forming a capacitor having a capacitance;
   a micromachined actuator for moving the probe electrode relative to the sample in response to an electrical drive signal to vary the separation which varies the capacitance;
   a dielectric part which mechanically connects and integrates the actuator and the probe tip but electrically insulates the actuator and the probe electrode, the dielectric part decoupling the electrical drive signal and the provided electrical signal from each other; and
   wherein the apparatus is a planar structure.

2. The apparatus as claimed in claim 1, wherein the actuator vibrates the probe electrode.

3. The apparatus as claimed in claim 1, wherein the planar structure includes a conductive foil.

4. The apparatus as claimed in claim 1, wherein the actuator and the probe electrode are formed by removing material from a sheet of material.

5. The apparatus as claimed in claim 4, wherein the sheet of material includes conductive foil and wherein the probe electrode and the actuator are formed by electric discharge machining the conductive foil.

6. The apparatus as claimed in claim 1, further comprising a substrate for supporting the actuator thereon.

7. The apparatus as claimed in claim 1, further comprising a signal lead connected to the probe electrode for conducting the provided electrical signal from the probe electrode.

8. The apparatus as claimed in claim 7, further comprising an electrical circuit coupled to the signal lead to measure the conducted electrical signal.

9. The apparatus as claimed in claim 8, wherein the electrical circuit includes a variable bias adjusted so that substantially no current flows between the sample and the probe electrode wherein the adjusted bias provides an indication of the surface potential of the sample.

10. The apparatus as claimed in claim 1, wherein the actuator includes an electrothermal actuator.

11. The apparatus as claimed in claim 10, wherein the electrothermal actuator is a bent-beam electrothermal actuator.

12. The apparatus as claimed in claim 1, wherein the dielectric part includes an epoxy plug.

* * * * *

UNITED STATES PATENT AND TRADEMARK OFFICE
CERTIFICATE OF CORRECTION

PATENT NO. : 7,116,115 B2  Page 1 of 1
APPLICATION NO. : 10/852058
DATED : October 3, 2006
INVENTOR(S) : Yogesh B. Gianchandani et al.

It is certified that error appears in the above-identified patent and that said Letters Patent is hereby corrected as shown below:

Column 1, lines 16-17 & Column 2 line 1, replace "DARPA under Grant No. 040074 and from NSF under Grant Nos. 043898 and DMR-0084402." to --National Science Foundation under Grant No. ECS0233174 and Air Force Research Laboratory under Grant No. F30602-00-1-0571.--

Signed and Sealed this

Tenth Day of April, 2007

JON W. DUDAS
*Director of the United States Patent and Trademark Office*